(12) United States Patent
Weisbuch et al.

(10) Patent No.: US 10,184,891 B2
(45) Date of Patent: Jan. 22, 2019

(54) BIOCHIP DEVICE

(75) Inventors: Claude Weisbuch, Paris (FR); Lucio Martinelli, Paris (FR); Henri Benisty, Palaiseau (FR); Christof Schafauer, Paris (FR); Gabriel Sagarzazu, Ciboure (FR); Thierry Gacoin, Bures sur Yvette (FR); Mélanie Bedu, Toulouse (FR)

(73) Assignee: GENEWAVE, Paris (FR)

( * ) Notice: Subject to any disclaimer, the term of this patent is extended or adjusted under 35 U.S.C. 154(b) by 478 days.

(21) Appl. No.: 13/976,596

(22) PCT Filed: Dec. 28, 2011

(86) PCT No.: PCT/FR2011/053208
§ 371 (c)(1),
(2), (4) Date: Oct. 7, 2013

(87) PCT Pub. No.: WO2012/089987
PCT Pub. Date: Jul. 5, 2012

(65) Prior Publication Data
US 2014/0017128 A1    Jan. 16, 2014

(30) Foreign Application Priority Data
Dec. 29, 2010    (FR) ..................... 10 61349

(51) Int. Cl.
*G01N 21/77* (2006.01)
*G01N 21/64* (2006.01)
(Continued)

(52) U.S. Cl.
CPC ........ *G01N 21/6428* (2013.01); *G01N 21/648* (2013.01); *G01N 21/6456* (2013.01)

(58) Field of Classification Search
None
See application file for complete search history.

(56) References Cited

U.S. PATENT DOCUMENTS

| 2004/0077099 A1* | 4/2004 | Yershov et al. ............... 436/164 |
| 2008/0019876 A1* | 1/2008 | Chau .................... G01N 21/554 422/82.05 |

(Continued)

FOREIGN PATENT DOCUMENTS

| DE | 196 11 025 | 9/1997 | ............. G01N 21/55 |
| FR | 2 832 506 | 5/2003 | ............. G01N 21/64 |

(Continued)

OTHER PUBLICATIONS

Sagarzazu et al., "Quantitative analysis of enhanced light irradiance in waveguide-based fluorescent microarrays," Biosensors and Bioelectronics, vol. 24, No. 7, Mar. 15, 2009, pp. 2281-2284.

(Continued)

*Primary Examiner* — Neil N Turk
(74) *Attorney, Agent, or Firm* — Young & Thompson

(57) ABSTRACT

A biochip device comprising a substrate constituted by at least one plate of material forming a multimode planar waveguide and carrying chromophore elements suitable for emitting fluorescence in response to excitation by guided waves having an evanescent portion, the device being characterized in that it includes coupling means for coupling excitation light with the waveguide in the form of guided waves, the coupling means being substantially non-directional.

20 Claims, 3 Drawing Sheets

(51) Int. Cl.
*G01N 21/47* (2006.01)
*G01N 21/55* (2014.01)

(56) References Cited

U.S. PATENT DOCUMENTS

| | | | |
|---|---|---|---|
| 2008/0246961 A1* | 10/2008 | Zhang et al. | 356/317 |
| 2008/0298740 A1* | 12/2008 | Hlousek | G01N 21/7743 385/12 |
| 2010/0055666 A1* | 3/2010 | Wimberger-Friedl et al. | 435/4 |
| 2010/0098592 A1* | 4/2010 | Rong et al. | 422/82.11 |
| 2011/0149286 A1* | 6/2011 | Wu | G01N 21/0303 356/436 |

FOREIGN PATENT DOCUMENTS

| | | | |
|---|---|---|---|
| FR | 2 846 745 | 5/2004 | G01N 21/64 |
| FR | 2 892 196 | 4/2007 | G01N 21/64 |
| FR | 2 932 885 | 12/2009 | G01N 21/64 |

OTHER PUBLICATIONS

Schmitt et al., "Optical Guided-wave Chemical and Biosensors I, High-Refractive-Index Waveguide Platforms for Chemical and Biosensing." Jan. 1, 2010, Optical Guided-Wave Chemical and Biosensors I, Springer Series on Chemical Sensors and Biosensors 7, pp. 21-54.
Bedu, "Développement de guides d'ondes planaires de $TiO_2$ optiquement actifs pour biopuces à ondes évanescentes," These De Doctorat, Mar. 1, 2010, Ecole Normale Superieure de Cachan, France, pp. 3-6, 36-37, 121-129 (figures IV-11), 134, 163-167 (figures V-13), 173-175.
International Search Report for International Application No. PCT/FR2001/053208, dated Jun. 4, 2012.

* cited by examiner

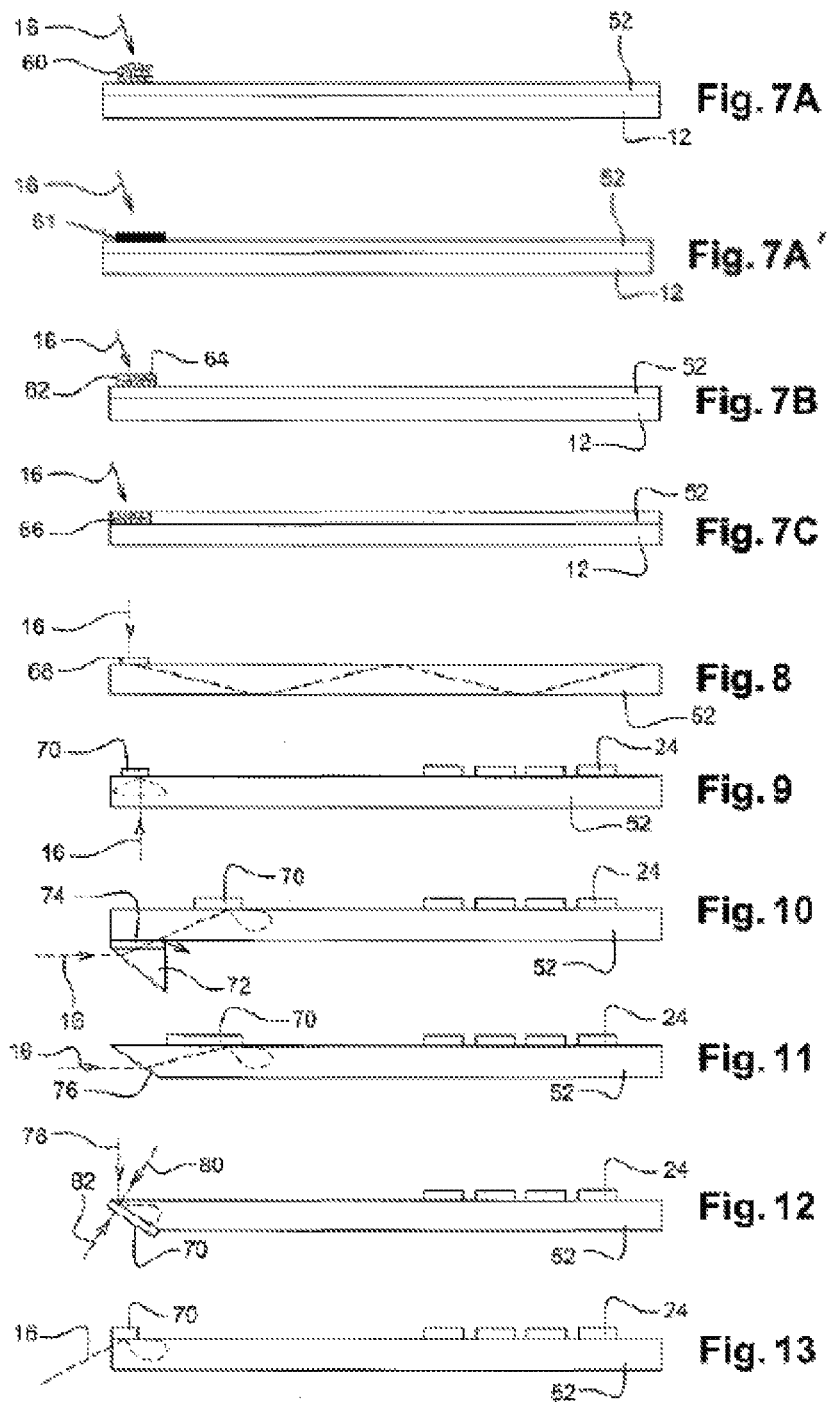

BIOCHIP DEVICE

BACKGROUND OF THE INVENTION

Field of the Invention

The invention relates to a biochip device for analyzing biological molecules by fluorescent marking.

Description of the Related Art

In such devices, a substrate includes pads constituted by probe molecules capable of hybridizing in preferential manner with target molecules contained in a hybridizing solution obtained from a sample to be analyzed. The target molecules are marked with the help of chromophore elements capable of emitting fluorescence with they are excited by appropriate light, the wavelength of the fluorescence depending on the nature of the chromophore elements.

After hybridizing, the biochip is dried and illuminated with a light source at the excitation wavelength of the chromophores marking the target molecules, and an image of the fluorescence of the biochip is picked up with the help of appropriate objects. In the image obtained in this way, the intensity of each point is associated with the quantity of chromophores present at the corresponding point of the biochip and thus associated with the number of target molecules that have been selectively fixed at that point during the hybridizing stage thus making it possible to obtain information about the biological species content of the hybridized solution.

That type of sequential reading of the fluorescence of the biochip after hybridizing is nevertheless unsuitable for performing real time reading of the hybridizing signal since the stages of hybridizing and of image taking are spaced apart in time, and take place in separate hybridizing and reading appliances.

Certain appliances are capable of performing both the hybridizing and the reading stages, thus making it possible to detect the signal in real time during the hybridizing stage (see in particular Y. Marcy, P.-Y. Cousin, M. Rattier, G. Cerovic, G. Escalier, G. Béna, M. Guéron, L. McDonagh, F. L. Boulaire, H. Benisty, C. Weisbuch, J.-C. Avarre, "Innovative integrated system for real time measurement of hybridization and melting on standard format microarrays" Biotechniques 44, 2008, 913). The image of the fluorescence of the pads carrying the hybridized molecules is acquired in the presence of the hybridizing liquid containing the target molecules that are marked, and thus fluorescent, and they may be present at high concentration. Fluorescence is then observed coming simultaneously from the target molecules attached to the pads of probe molecules (forming the useful signal) and from fluorescent molecules in the solution (constituting a background signal that is added to the useful signal).

That is disadvantageous, since the strong background signal generated by the fluorescent species in solution limits the sensitivity with which it is possible to detect the attachment of target molecules and limits the dynamic range over which hybridization can be measured.

In order to avoid that drawback, one possibility consists in selectively exciting the molecules at the surface of the biochip without exciting the molecules present in the solution, by using an evanescent wave at the surface of the biochip so as to excite only the fluorescent pads (one technique often used for that purpose is a configuration of the total internal reflection fluorescence (TIRF) type). By way of example, other evanescent wave excitation methods consist in using substrates carrying a waveguide, preferably a monomode waveguide, and in exciting one or more modes in the waveguide with the help of etched coupling gratings or in exciting guided modes in the biochip by lighting via an edge face (US 2004/077099 A1).

In general, it is also necessary to take into consideration the interaction between the guided waves and the optofluidic portion of the device in contact with the waveguide.

For the above-described evanescent wave devices, light coupling makes it necessary to use excitation devices having mechanical constraints that are very demanding in terms of precision.

That type of coupling makes it necessary either to use optical systems with sub-micrometer precision on polished edge faces for coupling the excitation light to a single mode, or else to have recourse to beams that are collimated with very precise angles (a few milliradians or less).

Nevertheless, it is known that incident light on non-uniform bodies such as metallic or dielectric particles, or more generally diffusers, make it possible to excite guided modes of any planar structure providing the elements of the diffuser are positioned very close to the waveguide, in the evanescent tail of the modes. This makes it possible to avoid the tight coupling tolerances encountered with the above-described devices. Such diffusers are referred to herein as "substantially non-directional means for generating or coupling guided modes".

The term "substantially non-directional coupling means" is used herein to designate means for coupling excitation light into the waveguide in the form of waves that are guided in a plurality of directions inside the waveguide by using excitation light coming from a plurality of directions. The excitation light may be coupled with the waveguide by using an excitation light beam that is not necessarily collimated. With such coupling means, there is no longer any need for the beam to be oriented very precisely relative to the waveguide.

Such coupling means are known for waveguides and solar cells, e.g. made of silicon. In those applications, a diffusing disordered interface serves to transform the incident light into guided light so that it is used in the waveguide or absorbed in the solar cell. For waveguide applications, the purpose is then to use the light in the waveguide so that it is absorbed therein, e.g. for use in a photodetector device. For solar cells, diffusion takes place over the entire surface of the cell in order to be able to capture all of the light intercepted by the cell.

An object of the invention is to provide a simple solution to the above-mentioned problems of biochip devices known in the prior art.

To this end, the invention provides a biochip device comprising a substrate constituted by at least one plate of material forming a multimode waveguide and carrying chromophore elements suitable for emitting fluorescence in response to excitation by guided waves having an evanescent portion, the device being characterized in that it includes coupling means for coupling excitation light with the waveguide in the form of guided waves, the coupling means being substantially non-directional.

Integrating substantially non-directional coupling means in a biochip device makes it possible to avoid the precision constraints encountered in the prior art.

In the invention, the coupling means cover only a portion of the biochip. In particular, the coupling means are placed at a distance from the fluidic or optofluidic portion so as to avoid extracting guided waves into the fluid containing fluorescent molecules, which is precisely what it is sought to avoid by exciting fluorophores that are excited by the evanescent waves only.

In an advantageous configuration, the device includes mode filter means for eliminating from the waveguide guided modes having an effective index less than or equal to a predetermined threshold value, this threshold value being selected so that no guided mode escapes from the waveguide beyond the zone having the mode filter means.

A first drawback of approaches based on substantially non-directional coupling means lies in the low efficiency of the coupling of the exciting modes with the guided modes. In order to reach a given guided mode intensity, it is possible to use an exciting source that is more intense. Nevertheless, the main drawback with a multimode waveguide is that that type of method of exciting guided modes tends to excite modes regardless of their effective index. Unfortunately, modes with smaller effective indices correspond to modes that leave the waveguide and penetrate into the fluid or into the optofluidic portions, where they contribute to increasing the background signal.

Because the guided modes transfer a propagating flux into the fluid only on contact with the fluid or the optofluidic portion, the use of non-directional coupling means can advantageously be combined with mode filter means that eliminate the unwanted modes that are capable of interacting with the fluid or the optofluidic portion.

From a theoretical point of view, the condition for non-transfer of a guided mode to an interface is conventionally presented in the form of an angle (angle of incidence at the interface being greater than a critical angle), however in more fundamental terms this condition can be expressed in the form of an effective index of the guided mode, which effective index must be greater than that of the fluid or of the optofluidic portion.

Generalizing from the above propositions, in the device of the invention, easy mechanical coupling is provided by means for generating guided waves that are low directional, such as optical diffusing media in particular, whereas the mode filter means serve to selectively filter out those of the guided modes that can be extracted from the waveguide and thereby increase the interfering background signal. Thus, the guided modes of effective index that is less than that of the material of the hybridizing chamber and than that of the biological solution are filtered out before they reach the optofluidic zone and a fortiori before they reach the zone carrying the chromophore elements, thereby avoiding exciting free chromophore elements in solution and out of reach of the evanescent wave.

BRIEF SUMMARY OF THE INVENTION

In a first embodiment, the mode filter means comprise an index-matching layer in contact with the waveguide and formed by a medium of index substantially equal to the predetermined threshold value so as to filter the guided modes of effective index less than the threshold value by extracting them, so that they do not reach the zones including fluidic or optofluidic functions. The index-matching layer determines the above-mentioned threshold value below which all previously-guided modes are extracted from the waveguide.

In a variant, the index-matching layer is interposed between the waveguide plate and an absorption bottom layer, the index-matching layer and the absorption layer extending substantially along the entire length of the waveguide, the absorption layer having an index not less than that of the index-matching intermediate layer and presenting absorption at the excitation wavelength of the chromophores that is considerable at the scale of the light path between the coupling means and a zone of the waveguide carrying the chromophore elements.

In practice, the absorption layer has an absorption coefficient that is greater than or equal to 2/L, where L corresponds to the distance between the non-directional coupling means and the optofluidic portion, in order to guarantee sufficient absorption of the modes that are of index less than the predetermined threshold value. These modes are caused to propagate in this layer and after a path length of about L they present transmission of less than exp(−2), which is approximately equal to 0.14. The waveguide plate and the index-matching layer make it possible with thicknesses known to the person skilled in the art to have at least one guided mode over at least one length L for which the index $n_{eff}$ is greater than the desired threshold.

In another variant of this first embodiment, the mode filter means are carried by the waveguide and are located between a zone of the waveguide in which the guided waves are generated and a zone of the waveguide carrying the chromophore elements.

Advantageously, absorption means or deflector means for absorbing or deflecting the guided modes extracted from the waveguide are placed on the index-matching layer, so that the extracted modes cannot reach the fluidic or optofluidic portions of the biochip.

By way of example, the absorption means consists in a wideband filter. The deflector means may consist in a prism or in a grating, these means being directly in contact with the index-matching layer.

According to another characteristic of the invention, the index-matching layer and the absorption means or the deflector means extend along the waveguide over a distance that is longer than the length that makes it possible for the guided mode for filtering that has the greatest effective index to interact at least once with the interface through which the modes are filtered. This distance is given by 2e×tanθ, where e is the thickness of the waveguide and θ is the reflection angle inside the waveguide and relative to the normal of the waveguide. With such a minimum extent for the mode filter means, it is guaranteed that all of the guided modes of effective index less than the predetermined threshold value are subjected at least to refraction or to absorption or to deflection at the interface with the waveguide and are thus extracted from the waveguide.

According to another characteristic of the invention, the mode filter means extend upstream from and outside the zone carrying the chromophore elements and also in part in said zone. This has the advantage of filtering photons that might have been diffused by the edges of the hybridizing chamber to produce guided modes in the waveguide of uncontrolled index that might subsequently leave the waveguide and excite the hybridizing solution.

Preferably, the threshold value is selected to be greater than or equal to the greatest refractive index of the elements constituting the environment of the chromophores, and that are generally in optical contact such as for example the elements constituting a hybridizing chamber placed on the substrate and a hybridizing fluid contained in the chamber, thereby avoiding any guided modes of effective index less than the threshold value being extracted from the waveguide and propagating directly into the hybridizing fluid, or else indirectly into the fluid via the material of the hybridizing chamber, where they would excite the chromophores of target molecules that are not attached to probe molecules.

In practice, the threshold value lies in the range n=1.30 to n=1.45 since the refractive index of a hybridizing solution generally lies in the range n=1.3 to n=1.4 and the material constituting the chamber is usually polydimethylsiloxane (PDMS) for which n=1.42.

In a second embodiment, the mode filter means are formed by the plate carrying the chromophore elements and having top and bottom faces that diverge from each other going from the zone of the coupling means to downstream from the zone carrying the chromophore elements, so as to raise the smallest effective index in the light being distributed on the occasion of each internal reflection. This thus corresponds to making the rays of the guided waves more oblique on reaching the optofluidic zone than the limit angle associated with passing into the fluid or into the material of the hybridizing chamber.

In this second embodiment, the structure is thus no longer planar but flared, with an angle a defined between the top and bottom faces of the above-mentioned plate. Thus, the angle of a guided mode therefore increases by 2α on each rebound of the guided mode from the bottom face. Applying the laws of geometrical optics to the successive images coming from a point on the top surface readily shows that the smallest angle (corresponding to the lowest effective index) increases up to the limit of 90° as the source generating guided waves approaches the edge formed by the intersection between the top and bottom faces of the waveguide. There therefore exists an ideal position between that edge and the optofluidic system for placing the substantially non-directional coupling means.

In a particular version of this second embodiment, the top and bottom faces of the waveguide are plane and the non-directional coupling means are placed at one-fourth of the distance between an edge formed by the intersection of the top and bottom faces and the portion of the waveguide carrying the chromophore elements.

In a possible variant, only the top face need be plane, it being possible for the bottom face to be curved and concave.

Preferably, the excitation light is coupled by diffusion and generates guided modes that propagate in a plurality of directions inside the waveguide.

The guided waves may be generated by illuminating a diffusing structure formed in or on the waveguide, thereby making it possible to form guided waves that propagate in a plurality of directions inside the waveguide, and avoiding a subsequent step of making the guided light uniform in the plane of the waveguide.

Advantageously, the diffusing structure used for providing substantially non-directional coupling is a structure having a disordered spatial distribution of index.

The diffusing structure may be formed by frosting with a typical grain size both in the plane of the waveguide and perpendicularly thereto lying in the range 0.1 micrometers (µm) to 50 µm. The diffusing structure may also be formed by a layer deposited on a face of the waveguide, e.g. a layer of "Teflon" or of metallic or colloidal particles.

In a variant, the diffusing structure may comprise diffusing particles in a matrix of a resin, e.g. such as an acrylic resin, a glycerophthalic resin, or a polymer, which may be a fluoropolymer. In order to guarantee good diffusion of the excitation light by the diffusing structure, it is preferable for the matrix to have a refractive index that is less than that of the diffusing particles by at least Δn=0.5. It is thus preferable to use particles of high index, e.g. oxides such as $TiO_2$, $Ta_2O_5$, $BaSO_4$.

The diffusing structure may also be situated inside the waveguide and may be made in the form of microcavities having dimensions of the order of 0.1 µm to 40 µm, and preferably of the order of 0.1 µm to 30 µm. It may also be made in the form of local modifications such as locally forming non-stoichiometric compounds of the $SiO_x$ type in glass, for example, or indeed in the form of molecular zones of phases different from the phase of the waveguide, e.g. ordered instead of amorphous, in particular. These stoichemetric changes or phase changes affect the index or the dielectric tensor of the diffusing structure. Such a diffusing structure may be made by localized energy delivery by using a laser focused on the point at which it is desired to form the diffusing structure.

In a second embodiment of the diffusing structure, the diffusing structure is deposited on a face of the waveguide and comprises a layer of fluorophore material and responds to light excitation by generating fluorescent light that propagates in turn in the waveguide in the form of waves having an evanescent portion.

The fluorophore materials may be of a very wide variety of kinds and in particular they may comprise quantum dots, organic fluorophores, or fluorophores based on rare earth or on luminescent ions.

BRIEF DESCRIPTION OF THE DRAWINGS

Other advantages and characteristics of the invention appear on reading the following description made by way of non-limiting example and with reference to the accompanying drawings, in which:

FIGS. 7A, 7A', 7B, and 7C are diagrams of the portion of the waveguide where guided waves are formed having an evanescent portion; and FIGS. 8 to 13 show various setups enabling guided waves to be generated in the waveguide with the device of the invention.

DETAILED DESCRIPTION OF THE PREFERRED EMBODIMENTS

Figure 1:
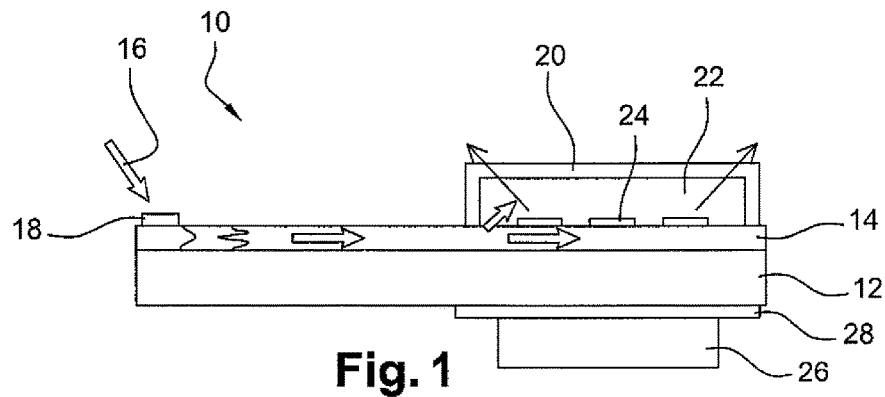
FIG. 1 is a diagrammatic section view of a prior biochip art device.

Reference is made initially to FIG. 1, which shows a prior art biochip device 10 comprising a substrate 12 including a top layer 14 forming a waveguide. An excitation light 16 is directed to coupling means 18, e.g. such as a grating formed on the surface of the waveguide so as to cause a guided wave to propagate inside the waveguide 14. At a distance from the grating 18, the waveguide 14 caries a hybridizing chamber 20 containing a solution 22 including target molecules marked by chromophore elements and suitable for hybridizing with probe molecules deposited on pads 24 on the surface of the waveguide 14.

Detector means are provided, e.g. on the face of the substrate 12 that is opposite from its face carrying the hybridizing chamber 20, and they comprise a camera 26 such as a charge coupled device (CCD) or a complementary metal oxide on silicon (CMOS) camera and a filter 28 for rejecting the light for exciting the chromophore.

In such a device, the evanescent portion of the guided wave excites the chromophores carried by the waveguide 14. Nevertheless, and as mentioned above, that type of device can be difficult to implement because of the difficulty of achieving appropriate optical coupling between the incident light and the waveguide, since the coupling requires great precision on the collimation angle of incidence of the excitation light if coupling is performed by a conventional resonant grating in guided optics, or else it requires submicron mechanical precision if the coupling is directly via the edge face. Furthermore, and above all, when the waveguide is suitable for having a plurality of guided modes propagate therein, i.e. a waveguide typically having a thickness greater than the wavelength of the guided waves for index steps of about 1, then guided waves having an effective index of less than the index of the elements surrounding the chromophores, such as the material of the hybridizing chamber 20 or the hybridizing solution 22, are extracted from the waveguide 14 and excite target molecules that are present in the hybridizing solution 22 but that are not attached to probe molecules. This results in a decrease in the signal-to-noise ratio when measurement of the luminescence emitted by the chromophores is performed in real time.

The device of the invention proposes using coupling means 19 that are substantially non-directional and of dimensions that are not very critical (e.g. 0.1 millimeter (mm) to 10 mm) providing optical coupling between the light source and the waveguide so as to generate waves that are guided in a plurality of directions inside the waveguide, e.g. from an excitation light beam that is not collimated. By way of example, such coupling means may be of diffusing structure and they are described in greater detail below in the description.

Advantageously, the coupling means are combined with mode filter means so as to extract from the multimode planar waveguide 14 those guided modes for which the effective index is less than or equal to a predetermined threshold value.

Figure 3:
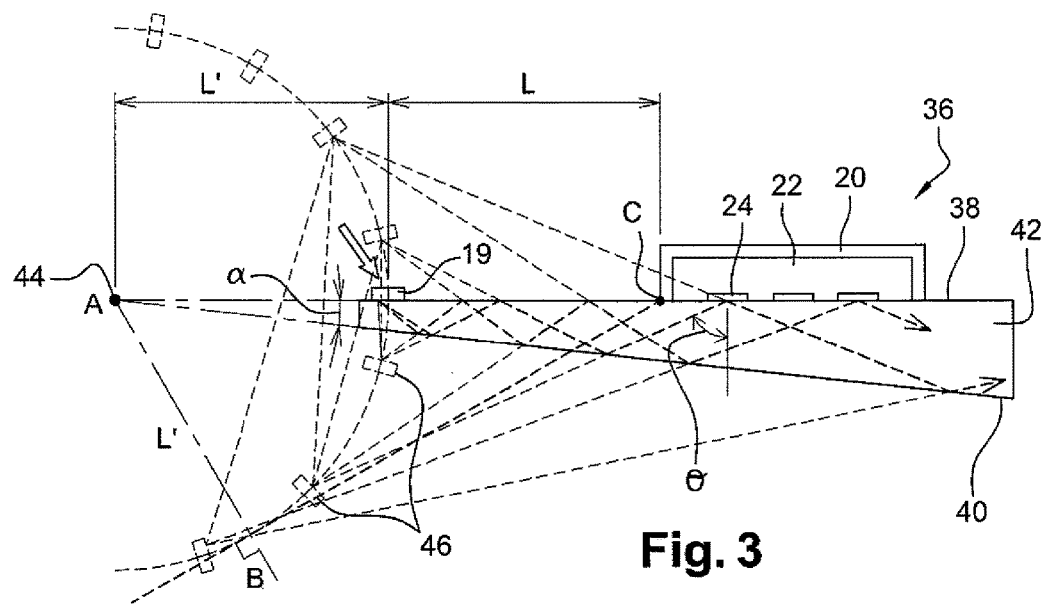
Figure 4:
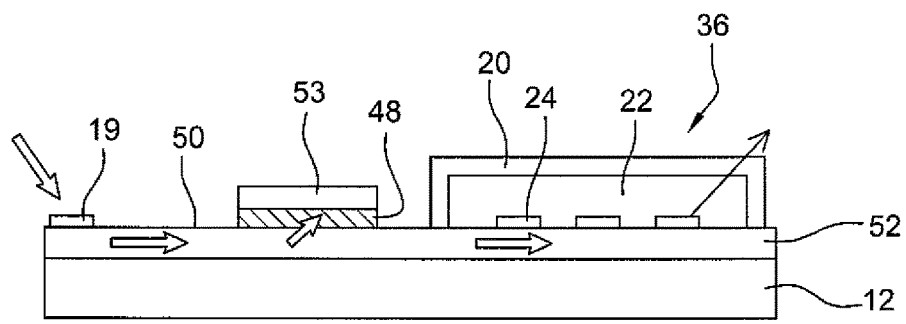
FIG. 4 is a diagrammatic section view of a biochip device of the invention in which the waveguide carries the mode filter means.
Figure 5:
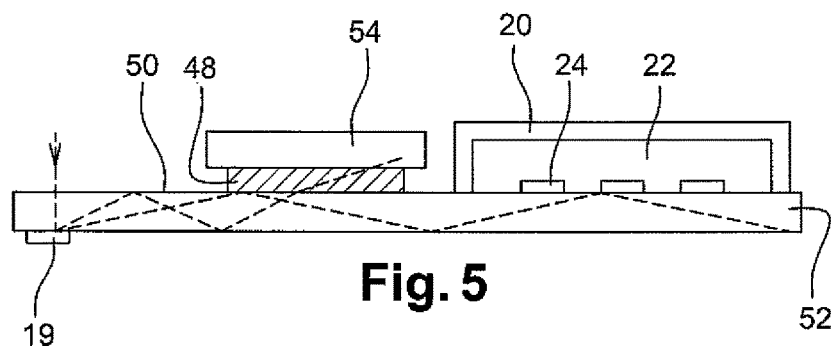
FIGS. 5 and 6 and diagrammatic section views of two variants of the FIG. 4 device.
Figure 6:
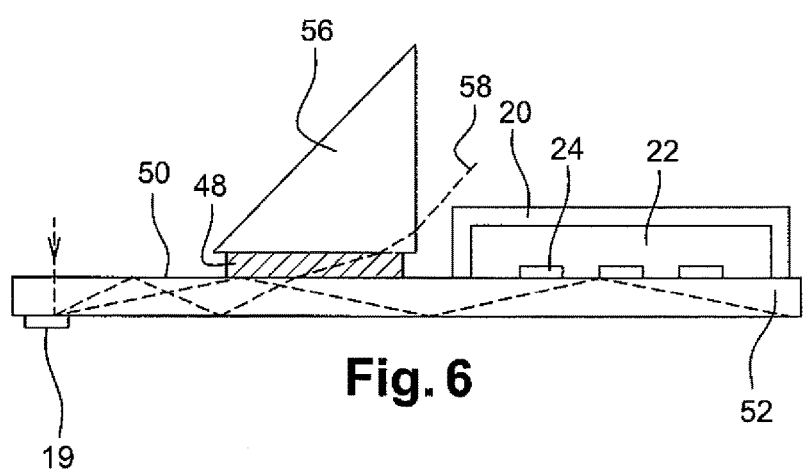

These mode filter means may either be formed by the waveguide itself (FIGS. 2 and 3) or else they may be carried thereby (FIGS. 4 to 6).

Figure 2:
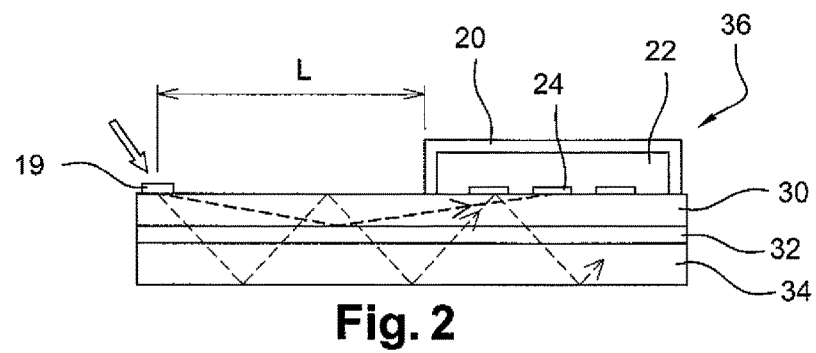
FIGS. 2 and 3 are diagrammatic section views of a biochip device of the invention including mode filter means integrated in the waveguide.

Reference is now made to FIG. 2, which shows a stratified structure comprising three superposed layers, with the top layer 30 serving as a planar waveguide without absorption and having an index $n_1$. The second layer 32 is interposed between the top layer 30 and an absorption bottom layer 34. The index-matching intermediate layer 32 has an index $n_2$ that is substantially equal to the predetermined threshold index value.

In this embodiment, the top layer 30 has the coupling means 19 at one end and has an optofluidic portion 36 at another end. The intermediate and absorption layers 32 and 34 extend over the entire length of the guiding top layer 30 so as to perform filtering over the entire length L between the substantially non-directional coupling means 19 and the optofluidic portion 36.

The index $n_3$ of the absorbent layer 34 is selected to be greater than $n_2$, while the thickness of the layer is appropriate in application of the rules of guided optics and $n_1$ is sufficiently large given the contrast firstly with $n_2$ and secondly with the index n of the hybridizing solution 22 to be capable of accepting at least one mode of index higher than the desired threshold. The thickness $z_2$ of the intermediate layer of index $n_2$ is sufficient to ensure that this mode does not escape over the distance L: the exponential decay factor in $z_2$, $$f = \exp[2 \times \pi \times (z_2/\lambda) \times \sqrt{n_{\mathit{eff}}^2 - n^2} > 1]$$

must be at least three times greater than the ratio $L/z_1$ of L to the thickness $z_1$ of the layer 30 of the index $n_1$ for the intermediate layer to perform its role over the length L. The modes of index $n_{\mathit{eff}} < n_2$ are obliged to propagate in the absorbent third layer of thickness $z_3$ and to travel a distance of about L therein. It then suffices to provide this third layer 34 with an absorption coefficient $\alpha_3$ that is greater than $2/L$ in order to attenuate the undesirable modes of index $n_{\mathit{eff}} < n_2$.

By way of example, these three stratified layers may be made of polymer. A typical index sequence may be $n_1=1.55$, $n_2=1.42$, and $n_3=1.55$. The thicknesses may be $z_1=5$ μm to 50 μm for the layer 30, $z_2>3$ μm for the layer 32, and $z_3$ greater than or equal to $z_1$ for the layer 34, e.g. being about 500 μm for a length L of 1 centimeter (cm). The absorption may be obtained by means of an organic or inorganic dye dispersed in the third layer 34. In practice, in order to absorb the light at a wavelength of 532 nanometers (nm) that is used for exciting chromophores such as Cyanine 3, it is possible to perform doping with absorbents that are stable, such as $Fe^{3+}$ salts of iron.

FIG. 3 shows a second embodiment of coupling means formed by the waveguide. In this embodiment, the top and bottom faces 38 and 40 of the waveguide 42 are plane and they diverge from each other going from the coupling means 19 towards the optofluidic portion 36, e.g. in the form of a wedge. The top and bottom faces 38 and 40 of the waveguide 42 form an angle α at the edge 44 where they intersect, which edge in the present example is situated outside the device. Such a waveguide 42 is referred to as a "wedge" waveguide. The light rays coming from the coupling means 19 that are reflected on the bottom face 40 become increasingly inclined relative to the top face 38, by an angle 2α for each pair of reflections. This filtering is "dynamic" filtering in which the energy of the modes is shifted to ever increasing effective indices as the light rays propagate.

In order to understand the operation of such filtering, it is possible to make use of the laws of geometrical optics. It is thus possible to predict that the successive images 46 of the coupling means 19 are turned through successive angles of 2α on each pair of reflections and that they move away towards the edge 44 by following a semicircle centered on the edge 44. This implies a limit on the angle of incidence that can be achieved at the optofluidic portion, as a function of the two pertinent distances in the geometrical optics problem, namely L' corresponding to the distance of the edge 44 from the coupling means 19, and the distance L from the coupling means 19 to the optofluidic portion 36. Constructing a right-angled triangle ABC with A at the edge 44 and of radius L' shows that the maximum angle of incidence θ of a light ray on the optofluidic portion is given by:

$$\sin(90°-\theta) = \cos\theta = L'/(L+L')$$

since the right-angled triangle ABC has the angle 90°−θ at the vertex C. Determining this angle thus requires a minimum value for the effective index that is given by $$n_{\mathit{eff}} = n \times \sin(\theta)$$

In practice, it is desirable to aim for angles θ of about 70° ($n_{\mathit{eff}}=1.41$ for a waveguide material having an index of about n=1.5). This imposes the following ratio:

$$L/L' = 1 - 1/\sin(90° - \arcsin(n_{\mathit{eff}}/n)) = 2$$

It should be observed that this result is independent of the angle α of the wedge. This angle may be selected in practice to lie in the range 2° to 10°. The overall extent of the coupling means 19, e.g. diffusers, needs to be taken into account, seeking merely to ensure that the desired condition applies for the most unfavorable of the light rays coming from said means, i.e. those from the source 19 that are the closest to the hybridizing chamber 20.

In other variants (not shown), the top and bottom faces may diverge from each other, but without being plane, as would be the case for example with curved faces that are concave. The top face may also be plane while the bottom face may be curved, for example it may present a concave curve.

In the embodiments shown in FIGS. 4 to 6, the filter means are carried by the waveguide and they are interposed between the coupling means 19 and the zone 36 of the waveguide 14 carrying the hybridizing chamber 20. Advantageously, these means comprise an index-matching layer 48 in contact with the top surface 50 of the waveguide 52. This index-matching layer 48 is selected so that its refractive index is equal to the predetermined threshold value (FIG. 4).

Means 53 for absorbing or deflecting the guided modes that are extracted from the waveguide 52 are advantageously placed on the index-matching layer 48.

In a practical embodiment of the invention, the absorption means may, for example, comprise a filter 54 having a wide absorption spectrum that performs volume filtering on the guided wave. This type of filter is very suitable since it reflects only very little of the guided light waves at its interface with the index-matching layer 48 (FIG. 5). The deflection means may, for example, comprise a prism 56 of index selected to deflect the extracted guided light waves as shown at 58 in FIG. 6.

Because of the presence of an index-matching layer between the coupling means and the zone 36 of the waveguide carrying the hybridizing chamber 20, the guided modes that are of effective index that is less than the index of the index-matching layer 48 are extracted from the waveguide and are refracted inside said layer. The presence of absorption means 54 or deflection means 56 on the layer 48 prevents any reflection of the guided modes that have been extracted via the top interface of the index-matching layer 48, which would lead to the extracted guided modes being re-introduced into the inside of the planar waveguide 52.

In order to guarantee optimum filtering of the guided modes of effective index less than the predetermined threshold value, the index-matching layer 48 and the absorption means or the deflection means must extend, between the zone 19 where the guided waves are generated and the zone 36 carrying the hybridizing chamber 20, over a distance that is greater than or equal to 2×e×tan θ, where e is the thickness of the waveguide and θ is the reflection angle inside the waveguide relative to the normal to the waveguide 52 for the guided mode for filtering that has the greatest effective index. In this way, it is possible to guarantee that all of the guided modes of effective index less than the predetermined threshold value are subjected to at least one reflection at the interface between the waveguide 52 and the index-matching layer 48.

In a variant, the mode filter means may also extend at least in part under the pads 24 in the hybridizing chamber so as to filter out the photons that the edges of the chamber might diffuse towards uncontrolled index modes of the waveguide that could then escape and excite the solution.

In an embodiment of the invention, the hybridizing chamber 20 is made of polydimethylsiloxane (PDMS) having a refractive index n=1.42, and the hybridizing solution 22 is water-based having an index of about n=1.33. Under such circumstances, the index-matching medium 36 is selected to have an index that is not less than the highest index in the environment of the chromophores, i.e. n=1.42.

In practice, the threshold index value is selected to lie in the range n=1.30 to n=1.45, which corresponds to the index values commonly encountered for the materials of the hybridizing chamber 20 and also for the hybridizing solution 22.

There follows a more detailed description of the means used for generating a plurality of guided waves inside the planar waveguide and having an evanescent portion for exciting the chromophore elements fixed to the pads 24.

In a first embodiment, the device has a diffusing structure formed in the waveguide or on the waveguide and that is to be illuminated by the excitation light.

This diffusing structure (FIGS. 7 and 8) presents a disordered spatial distribution of index so as to diffuse the excitation light into the waveguide in a plurality of directions. Such a structure makes it easier to convert the excitation light into guided light and to do so with efficiency that depends little on the excitation conditions, and in particular on the angle of incidence. Thus, with such a diffusing structure, the angle of tolerance is quite large, being about 10 degrees, which does not require a high precision mechanical and optical setup, as compared with tolerance of about 0.1 degrees when using a grating 18.

This diffusing structure may be on one or other of the faces of the waveguide 14 that is transparent to the excitation light 16.

In a first embodiment of the diffusing structure 60, it is constituted by a layer deposited on the waveguide and presenting an internal structure that is disordered. The layer may consist in a deposit of metallic or colloidal particles 60 (FIG. 7A), or indeed a deposit of "Teflon" (polytetrafluoroethylene).

It is also possible to deposit a layer 62 made up of a matrix containing diffusing particles 64 (FIG. 7B). The matrix may consist in a resin of the same type as that used for paints or varnishes, such as for example acrylic resins or glycerophthalic resins or indeed fluoropolymers.

In order to guarantee good conversion by diffusion of the excitation light 16 into guided waves with a thin diffusion layer, i.e. a diffusion layer with a thickness of about 15% to 60%, it is desirable for the refractive index of the matrix to be less that the index of the diffusing particles 64 by at least Δn=0.5.

A diffusing structure 66 may also be obtained by making microcavities (FIG. 7C), e.g. spheroidal microcavities, inside the waveguide 14 or by locally modifying the material of the waveguide 14 by changing its degree of oxidation or by changing its phase, from amorphous to crystalline or from crystalline to amorphous, e.g. by means of laser pulses having a duration lying in the range 0.1 picoseconds (ps) to 1 microsecond (ps) with typical energy lying in the range 1 nanojoule (nJ) to 100 to microjoules (pJ). This type of structure thus presents index discontinuities suitable for diffusing the excitation light in a plurality of directions. There also exist methods of nucleating pores in a sol-gel phase, and these methods are often used for making layers of low dielectric constant in microelectronics.

In another embodiment of a diffusing structure, it consists in a layer 68 of fluorescent and diffusing material such as the phosphors of white light-emitting diodes (LEDs) that respond to light excitation by generating guided waves having an evanescent portion and propagating in a plurality of directions.

The fluorescent material may consist in an ordered or disordered layer of fluorophores, in particular such as those based on quantum dots, organic fluorophores, or fluorophores based on rare earth.

The layer of fluorescent material may also consist in a layer comprising a binder such as an organic or inorganic powder with grain size lying in the range 0.1 µm to 50 µm or a polymer matrix belonging to the families used for makeup and for paint and varnishes, such as acrylic resins, glycerophthalic resins, etc., and fluorophore elements such as those described in the paragraph above.

The layer of fluorescent material may also include diffusing elements of the high-index particle type (e.g. oxides of titanium or carbonates of calcium or barium sulfate) and fluorophores such as those mentioned above.

With the diffusing structure made in these ways, the process of creating guided light waves possessing an evanescent portion may be thought of as emitting a set of optical dipoles at the surface of the waveguide or inside it. With a diffusing structure as shown in FIGS. 7A, 7B, and 7C, these dipoles oscillate at the same frequency as the excitation light 16, and with a structure that diffuses by fluorescence, the dipoles oscillate after frequency conversion at the frequency at which the fluorophores fluoresce. Under such circumstances, the fluorescence frequency is selected so as to be suitable for exciting the chromophores carried by the pads 24.

The diffusing structure may be excited by the light 16 either directly or indirectly, as shown in FIGS. 8 to 13.

FIG. 8 shows excitation of the diffusing structure by transmission of the excitation light 16 through the diffusing structure 68. This is possible only when the diffusing structure 68 presents little opaqueness in order to avoid the excitation light 16 being absorbed by the diffusing structure 68.

FIG. 9 shows the diffusing structure being excited by the excitation light 16 being transited through the thickness of the waveguide.

In another configuration, shown in FIG. 10, a prism 72 may be optically coupled to the waveguide 52 via an index-matching layer 74. It is also possible for the prism 72 to be integrated with the waveguide 52 by molding. The excitation light 16 is thus deflected by the prism into the inside of the waveguide and it excites the diffusing structure 70.

In a similar embodiment, shown in FIG. 11, a chamfer 76 is made at the end of the waveguide that carries the diffusing structure 70. For the two embodiments shown in FIGS. 10 and 11, the excitation light 16 is oriented parallel to the plane of the waveguide towards the sloping surface of the prism 72 or of the chamfer 76. The light 16 is then deflected towards the diffusing structure 70 in order to generate guided light waves having an evanescent portion.

In the embodiment of FIG. 12, the diffusing structure 70 is carried by the chamfered surface 62 of the waveguide and the excitation light may be at any orientation relative to the plane of the waveguide carrying the pads 24. The excitation light 78 may thus be oriented perpendicularly to the plate or it may be inclined relative to the vertical to the plate (as shown at 80). It passes through a portion of the waveguide in order to illuminate the diffusing structure. The excitation light 82 may also excite the waveguide by diffusion/transmission through the diffuser 70.

In a last embodiment, shown in FIG. 13, the excitation light 16 is transmitted to the diffusing structure 70 through the polished or unpolished edge face of the waveguide 14.

The invention claimed is:

1. A biochip device for excitation by an excitation light having a wavelength, the biochip device comprising:
a multimode waveguide that is a plate of material having a refractive index, with a thickness in a range supporting multiple light-propagating modes at the excitation wavelength, the multimode waveguide having a top face and a bottom face, the multimode waveguide having a portion carrying chromophore elements emitting fluorescence in response to the excitation light by guided waves having an evanescent portion, the chromophore elements being used to detect molecular attachments; and
a light-diffusing element configured to diffuse the excitation light incoming from a direction out of the plane of the waveguide into the waveguide in a plurality of modes propagating inside the waveguide in the plane of the waveguide as guided waves and having a disordered spatial distribution of refractive index, the light-diffusing element diffusing the excitation light into the waveguide from another portion of the waveguide to the portion carrying the chromophore elements, the light-diffusing element being a light diffusing structure provided in the waveguide or on the waveguide, or being modifications of the waveguide,
the light diffusing structure comprising one of non-uniform metal or dielectric particles or colloidal particles positioned in the waveguide or on the top face or the bottom face of the waveguide, microcavities formed within the waveguide, and a layer of polytetrafluoroethylene on the waveguide,
the modifications being one of non-stoichiometric compounds and local phases of the waveguide being different from the phase of remaining portions of the waveguide.

2. The device according to claim 1, further comprising an index-matching layer disposed on the top face or the bottom face of the waveguide, the index-matching layer having a refractive index smaller than the refractive index of the waveguide material.

3. The device according to claim 2, further comprising, a means for absorbing light, the index-matching layer interposed between the top face or the bottom face of the waveguide and the means for absorbing light, the index-matching layer and the means for absorbing light together eliminating guided modes from the waveguide.

4. The device according to claim 3, wherein the index-matching layer is carried by the waveguide and is located between the light-diffusing structure and said portion of the waveguide carrying the chromophore elements.

5. The device according to claim 4, wherein means for absorbing is disposed on the index-matching layer.

6. The device according to claim 2, a means for deflecting light placed on the index-matching layer.

7. The device according to claim 6, wherein the means for deflecting comprises a prism.

8. The device according to claim 3, wherein said waveguide has a thickness e and a guided mode having the greatest effective index reflecting inside the waveguide has a reflection angle θ, and
the index-matching layer and the absorption layer extend over a distance that is longer than 2×e×tanθ.

9. The device according to claim 2, wherein the index-matching layer extends upstream from the portion carrying the chromophore elements and in part within said portion.

10. The device according to claim 1, wherein the waveguide is a wedge waveguide that has top and bottom faces and a side edge connecting the top and bottom faces, the top and bottom faces diverging from each other from a point going from the light-diffusing structure to downstream from the portion of the biochip device carrying the chromophore elements, the side edge being opposite the point.

11. The device according to claim 2, further comprising a hybridizing chamber disposed on the top face of the waveguide and surrounding the portion of the waveguide carrying the chromophore elements and a hybridizing fluid contained in said chamber, wherein the refractive index of the index-matching layer is greater than or equal to the greatest refractive index of said hybridizing chamber and said hybridizing fluid.

12. The device according to claim 11, wherein the value of the refractive index of the index-matching layer lies in the range n=1.30 to n=1.45.

13. The device according to claim 1, wherein the non-uniform metal or dielectric particles are particles in a resin or polymer matrix having a refractive index that is less than that of the diffusing particles by at least 0.5.

14. The device according to claim 1, wherein the light-diffusing structure comprises the microcavities that are sized from 0.1 µm to 40 µm.

15. The device according to claim 1, wherein the light-diffusing structure is the non-uniform metal or dielectric particles, and the non-uniform metal or dielectric particles are deposited on one of the faces of the waveguide and comprise fluorophore material that responds to light excitation by generating fluorescent light that propagates in the waveguide in the form of waves having an evanescent portion.

16. The device according to claim 15, wherein the fluorophore material comprises quantum dots, organic fluorophores, or rare earth or luminescent ions.

17. The device according to claim 6, wherein said waveguide has a thickness e and a guided mode having the greatest effective index reflecting inside the waveguide has a reflection angle $\theta$, and the index-matching layer and the absorption structure extend over a distance that is longer than $2 \times e \times \tan\theta$.

18. The device according to claim 1, wherein the light-diffusing structure that is one of the non-uniform metal or dielectric particles or the polytetrafluoroethylene is formed by a layer deposited on one of the faces of the waveguide.

19. The device according to claim 13, wherein said matrix is made of an acrylic resin or of a glycerophthalic resin.

20. The device according to claim 13, wherein said matrix is a fluoropolymer matrix.

* * * * *